US010172707B2

(12) United States Patent
Niklason et al.

(10) Patent No.: US 10,172,707 B2
(45) Date of Patent: Jan. 8, 2019

(54) TUBULAR PROSTHESES

(71) Applicants: HUMACYTE, INC., Research Triangle Park, NC (US); YALE UNIVERSITY, New Haven, CT (US)

(72) Inventors: Laura Niklason, Greenwich, NC (US); Angela Huang, New Haven, CT (US); Liping Zhao, New Haven, CT (US); Shannon Dahl, Durham, NC (US)

(73) Assignees: Humacyte, Inc., Research Triangle Park, NC (US); Yale University, New Haven, CT (US)

(*) Notice: Subject to any disclaimer, the term of this patent is extended or adjusted under 35 U.S.C. 154(b) by 838 days.

(21) Appl. No.: 14/351,408

(22) PCT Filed: Oct. 12, 2012

(86) PCT No.: PCT/US2012/059955
§ 371 (c)(1),
(2) Date: Apr. 11, 2014

(87) PCT Pub. No.: WO2013/056049
PCT Pub. Date: Apr. 18, 2013

(65) Prior Publication Data
US 2014/0330377 A1 Nov. 6, 2014

Related U.S. Application Data

(60) Provisional application No. 61/547,350, filed on Oct. 14, 2011.

(51) Int. Cl.
*A61F 2/20* (2006.01)
*A61L 27/36* (2006.01)
(Continued)

(52) U.S. Cl.
CPC ............ *A61F 2/20* (2013.01); *A61L 27/3633* (2013.01); *A61L 27/3679* (2013.01);
(Continued)

(58) Field of Classification Search
CPC ...................................................... A61K 45/00
(Continued)

(56) References Cited

U.S. PATENT DOCUMENTS

| 2002/0115208 | A1 | 8/2002 | Mitchell et al. |
| 2005/0013870 | A1* | 1/2005 | Freyman ............ A61L 27/3633 424/520 |

(Continued)

FOREIGN PATENT DOCUMENTS

WO 2012094611 A1 7/2012

OTHER PUBLICATIONS

Basu J et al: "Platform technologies for tubular organ regeneration", Trends in Biotechnology, Elsevier Publications, Cambridge, GB, vol. 28, No. 10, Oct. 1, 2010 (Oct. 1, 2010), pp. 526-533.
(Continued)

*Primary Examiner* — Yashita Sharma
(74) *Attorney, Agent, or Firm* — Banner & Witcoff, Ltd.

(57) ABSTRACT

Tubular prostheses are provided for use in airways, upper digestive, and urinary tracts. Each of these uses has its own specific sets of biological specifications, based on what it must contain and exclude and the physical and chemical pressures and stresses to which it is subjected. The prostheses may be made from allogeneic cells. Thus they can be manufactured and stored prior to an individual's personal need arising.

11 Claims, 22 Drawing Sheets

(51) Int. Cl.
  *A61L 27/38* (2006.01)
  *A61L 27/48* (2006.01)
  *A61F 2/04* (2013.01)

(52) U.S. Cl.
  CPC ....... *A61L 27/3687* (2013.01); *A61L 27/3826* (2013.01); *A61L 27/3882* (2013.01); *A61L 27/48* (2013.01); *A61F 2002/046* (2013.01); *A61L 2430/22* (2013.01); *A61L 2430/40* (2013.01)

(58) Field of Classification Search
  USPC .................................. 623/1.15, 9; 424/93.7
  See application file for complete search history.

(56) References Cited

U.S. PATENT DOCUMENTS

| | | | | |
|---|---|---|---|---|
| 2005/0191281 | A1* | 9/2005 | Ollerenshaw | A61F 2/04 424/93.7 |
| 2013/0006349 | A1* | 1/2013 | Chun | A61F 2/06 623/1.15 |
| 2015/0030657 | A1* | 1/2015 | Ludlow | A61L 27/3826 424/424 |

OTHER PUBLICATIONS

Park et al: "Small Intestinal Submucosa Covered Expandable Z Stents for Treatment of Tracheal Injury: An Experimental Pilot Study in Swine", Journal of Vascular and Interventional Radiology, VA, Amsterdam, NL, vol. 11, No. 10, Nov. 1, 2000 (Nov. 1, 2000), pp. 1325-1330.

Koji Kojima et al.: "Autologous Tissue-Engineered Trachea With Sheep Nasal Chondrocytes", The Journal of Thoracic and Cardiovascular Surgery, vol. 123, 2002, pp. 1177-1184.

Kitagami et al.: "Experimental Study of Tracheal Patch Reconstruction With a Covered Expandable Metallic Stent", Ann Thoracic Surg., vol. 66, 1998, pp. 1777-1781.

Maurizio Marzaro et al.: "In Vitro and in Vivo Proposal of an Artificial Esophagus", Journal of Biomedical Materials Research Part A, vol. 77A, No. 4, 2006, pp. 795-801.

Zani A et al: "Tissue engineering: an option for esophageal replacement?", Seminars in Pediatric Surgery, Saunders, Philadelphia, PA, US, vol. 18, No. 1, Feb. 1, 2009 (Feb. 1, 2009), pp. 57-62.

Wang C et al: "A small diameter elastic blood vessel wall prepared under pulsatile conditions from polyglycolic acid mesh and smooth muscle cells differentiated from adipose-derived stem cells", Biomaterials. Elsevier Science Publishers, BV., Barking. GB., vol. 31, No. 4, Feb. 1, 2010 (Feb. 1, 2010), pp. 621-630.

Heather L Prichard et al: "An Early Study on the Mechanisms that Allow Tissue-Engineered Vascular Grafts to Resist Intimal Hyperplasia", Journal of Cardiovascular Translational Research, Springer US, Boston, vol. 4, No. 5, Jul. 12, 2011 (Jul. 12, 2011), pp. 674-682.

Poh M et al: "Blood vessels engineered from human cells", The Lancet, Lancet Limited. London, GB, vol. 365, No. 9477, Jun. 18, 2005 (Jun. 18, 2005), pp. 2122-2124.

Niklason L E et al: "Functional arteries grown in vitro", Science, American Association for the Advancement of Science. Washington, DC; US, vol. 284, No. 5413, Apr. 16, 1999 (Apr. 16, 1999), pp. 489-493.

International Search Report and Written Opinion dated Apr. 12, 2013, for PCT/US2012/059955.

Zhao et al., "Engineered Tissue-Stent Biocomposites as Tracheal Replacements," Tissue Engineering: Part A, vol. 22, Nos. 17 and 18, 2016, pp. 1086-1097.

* cited by examiner

TUBULAR PROSTHESES

TECHNICAL FIELD OF THE INVENTION

This invention is related to the area of artificial replacements for diseased or damaged anatomical conduits. In particular, it relates to conduits of fluids, solids, and gasses.

BACKGROUND OF THE INVENTION

Currently, there are about 2,000 patients per year in the U.S. who need replacement tracheal tissue. Causes for this include tracheal cancer, invasive infections of the trachea or bronchi, and trauma. There are no replacements currently available for trachea in humans. At best, when a segment of trachea is resected, the only surgical option is to "pull together" the two ends of the trachea and sew them together, hoping that the anastomosis does not "pull apart" thereafter.

Currently in the U.S., approximately 4,000 patients per year need an esophageal replacement. This is due primarily to esophageal cancer, though trauma and infection are causes a small number of cases of esophageal replacement. Currently, there is no available replacement for esophageal tissue. What is done currently to replace esophagus is one of two procedures. Either a segment of the stomach is loosened from its connections in the abdomen and brought up into the chest, to anastomose to the remnant esophagus; or, a segment of large bowel (i.e., colon) is resected from the patient and sewn in to replace the resected esophageal tissue. Both of these procedures have many complications and a viable esophageal replacement is certainly medically needed.

Every year in the U.S., approximately 10,000 patients undergo cystectomy, and require a urinary conduit to drain urine outside the body [Healthcare Cost and Utilization Project, N.I.S., 2007.]. In almost all cases, bowel is harvested from the patient to form either a noncontinent urinary diversion, or a continent urinary diversion that is catheterized intermittently to drain urine through a continent stoma. [Konety, B. R., Joyce, G. E., Wise, M., *Bladder and upper tract urothelial cancer*. Journal of Urology, 2007. 177: p. 1636-1645.]. Due to surgical simplicity and lower complication rates, creation of a noncontinent urinary conduit is the most common approach for draining urine following cystectomy. Most typically, a 15-25 cm length of ileum is harvested from the patient for use as the urinary conduit, and the remaining bowel is reanastomosed [Gudjonsson, S., Davidsson, T., Mansson, W., *Incontinent urinary diversion*. BTU International, 2008. 102: p. 1320-1325.]. One end of the harvested ileal segment is anastomosed to the patient's ureters, and the other end is then brought out to the skin to form a stoma through which urine can drain.

Though widely used, ileal conduits pose many problems that can lead to short-term and long-term complications [Konety, Allareddy, V., *Influence of post-cystectomy complications on cost and subsequent outcome*. Journal of Urology, 2007. 177: 280-287.]. In the short term, patients may suffer from complications at the bowel harvest site, including anastomotic leaks and peritonitis. In addition, ileal urinary conduits may suffer from ischemia and necrosis, which can lead to perforation, anastomotic breakdown, and leakage of urine from the conduit. In the long term, many patients suffer from chronic hyperchloremic metabolic acidosis, due to resorption of urine electrolytes through the conduit wall. Since ileal conduits harbor bacteria, patients also commonly suffer from recurrent urinary tract infections and pyelonephritis, as bacteria from the conduit infect the more proximal urinary system. Hence, there is a significant medical need for an improved method for urinary diversion, that avoids many of the complications associated with the use of Heal conduits [Dahl, D. M., McDougall, W. S., Campbell-Walsh Urology, 9th Edition: Use of intestinal segments and urinary diversion, ed. A. J. Wein, Kavoussi, Novick, A. C. 2009].

There is a continuing need in the art tier replacements for these important conduits, as well as other tubular tissues in the body, such as ureters, urethras, intestine, etc.

SUMMARY OF THE INVENTION

According to one aspect of the invention an artificial airway is provided for replacement of damaged or diseased tissue by implantation into a respiratory tract of a recipient. The artificial airway comprises a tubular stent and substantially acellular, non-layered, contiguous, extracellular matrix surrounding the stent on its inner and outer surfaces.

According to another aspect of the invention a method is provided of making an artificial airway. A tubular stent having an inner and outer surface is encased in at least two layers of a mesh scaffold. A first of the two layers is on the interior surface, and a second of the two layers is on the exterior surface. The mesh scaffold is seeded with vascular smooth muscle cells, which are then cultured on the mesh scaffold in a bioreactor for 6-10 weeks. The smooth muscle cells proliferate and secrete extracellular matrix on the mesh scaffold. The tubular stent is decellularized to form an acellular tubular airway stent encased in extracellular matrix on the inner and outer surfaces.

Another aspect of the invention is an artificial esophagus for replacement of damaged tissue by implantation. The esophagus comprises substantially acellular extracellular matrix formed as a tube of greater than 10 mm diameter. The artificial esophagus has a suture retention of greater than 150 grams.

Yet another aspect of the invention is an artificial urinary conduit for implantation in a patient in need of urinary diversion and drainage. The conduit comprises a tubular, substantially acellular, extracellular matrix formed as a tube of greater than 10 mm diameter. The extracellular matrix is produced and secreted by non-autologous smooth muscle cells. The artificial urinary conduit has a rupture strength of greater than 1000 mm Hg.

Yet another aspect of the invention is an artificial urinary conduit for implantation in a patient in need of urinary diversion and drainage. The conduit comprises a tubular, substantially acellular, extracellular matrix formed as a tube, as well as a tubular stent. The extracellular matrix is produced and secreted by non-autologous smooth muscle cells. The artificial urinary conduit has a rupture strength of greater than 1000 mm Hg.

These and other embodiments which will be apparent to those of skill in the art upon reading the specification provide the art with new surgical tools tier repairing damaged anatomical conduits.

BRIEF DESCRIPTION OF THE DRAWINGS

FIG. 3A: photograph of outside of engineered trachea, showing smooth tissue covering entire external surface. FIG. 3B: photograph of inside of engineered trachea, showing smooth tissue covering entire inner surface.

FIG. 8A: H&E stain of engineered esophagus shows cellular nuclei (purple) and extracellular matrix (pink). Scale bar is 50 microns. FIG. 8B: Masson's trichrome stain shows blue collagen in engineered esophagus, nuclei of cells appear red. Scale bar is 50 microns. FIG. 8C: Masson's trichrome stain of decellularized engineered esophagus, red nuclei are absent indicating loss of cells. Scale bar=50 microns.

FIG. 12A shows a gross photo of a 6-mm conduit after harvest from bioreactor and decellularization. FIG. 12B shows scanning electron microscopy image of an acellular conduit, showing smooth luminal surface and pores within the wall. FIG. 12C shows conduit pressurized to 100 mm Hg, which shows no leaks to liquid and an excellent kink radius of no greater than 1.5 cm.

FIG. 13A: gross photograph of aortocaval graft in a baboon; FIG. 13B: immunostaining for alpha-actin, a smooth muscle marker, shows smooth muscle cells infiltrating into the graft (g); FIG. 13C: T-cell proliferation in response to graft conduit is less than to control, teflon.

FIG. 14A shows a bioresorbable mesh scaffold surrounding a stent on its external surface. FIG. 14B shows a bioresorbable mesh scaffold on the interior surface of a stent. FIG. 14C shows a bioresorbable mesh scaffold placed on both the interior and the exterior surfaces of the stent, FIG. 141) shows the two layers described in FIG. 14C which have been stitched together to unify the two layers. FIG. 14E shows cells (white) which have been seeded on the mesh. FIG. 14F shows matrix (grey) which has been synthesized and secreted by the seeded cells. FIG. 14G shows an acellular matrix enveloping the stent after the cells have been removed by decellularization process.

DETAILED DESCRIPTION OF THE INVENTION

Figure 1:
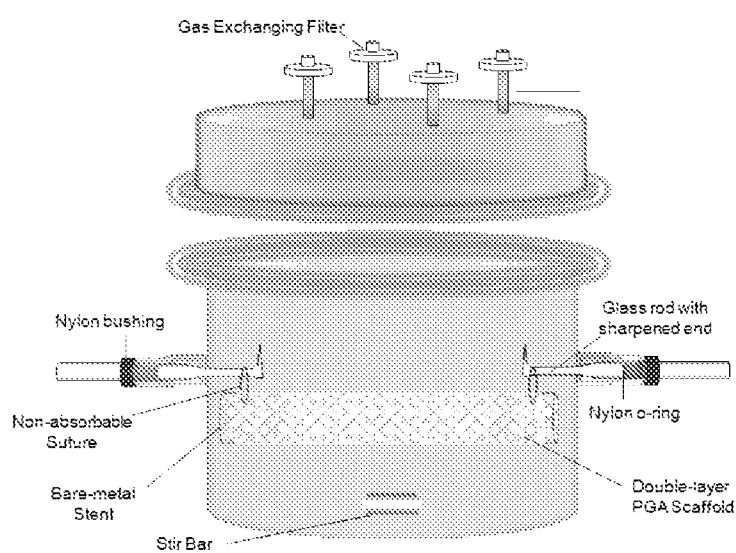
FIG. 1: to Schematic of placement of stent with surrounding PGA scaffold inside of bioreactor, in preparation for culture.

The inventors have developed new surgical tools for repairing damaged anatomical conduits, including airways, upper digestive tract, and urinary conduits. Because the conduits are formed by seeding cells on a tubular substrate, rather than as sheets which are subsequently wound to form a tube, or tubes that are layered, they are not subject to the risks of slippage or leakage can arise with a layered approach. Furthermore, no slippage or leakage occurs between the tissue and the tubular substrate (e.g., stent) because the tubular substrate or stent is integrated within the non-layered tissue. Moreover, there is no risk of unwinding of tissue layers. The conduits form a composite artificial tissue in which, in some embodiments, a stent is totally enveloped and encased within extracellular matrix that has been grown and secreted in situ. The extracellular matrix is a naturally occurring matrix that is produced by cells. The matrix is, preferably, not a denatured or chemically processes material, such as gelatin (which is denatured collagen) or proteins that are cross-linked by artificial processes such as freezing, or drying, or gluteraldehyde or other chemical fixation. The naturally occurring extracellular matrix that is produced by living cells is preferable for the practice of the current invention because it is more readily remodeled by host cells after implantation, and because it is less likely to induce adverse host responses such as inflammation or calcification as compared to denatured, processed, or artificially cross-linked extracellular matrices. Because of its mode of manufacture, no gaps exist or form during and after implantation. The conduits are in effect composite tissues. The tissues may be a composite of cells and matrix (decellularized), polymer fragments, and an optional stenting material. The extracellular matrix may, for example, bridge stent struts and completely incorporate the stent material.

The tissues so formed have matrix (ECM) that fits "snugly" around the stent struts. The tissues adjoin, are connected with, abut, are next to, have a common boundary touch, are contiguous with, share a common border with the stent. They form a unitary composite tissue that is not subject to separation and deconvolution into constituent parts.

Cells used in the conduits can be allogeneic, autologous, syngeneic, or xenogeneic. Typically cells used in making the conduits are killed and/or removed prior to use. The killing and/or removal of cells diminishes the potential for adverse immune reactions. Killing and/or removal of cells leaves less than 50%, less than 75%, less than 80%, less than 85%, less than 90%, or less than 95% of the cells viable, as assessed by trypan blue staining, nucleotide incorporation, or protein synthesis. Remaining extracellular matrix is highly conserved among individuals, and among species, rendering it less likely to provoke an adverse immune reaction than live cells. Vascular smooth muscle cells are one type of cell that can be used to make the extracellular matrix. These can be isolated from any vasculature of a human or other mammal, including from the aorta. Much of the secreted extracellular matrix comprises collagen. Collagen may comprises at least 5%, at least 10%, at least 15%, at least 20%, at least 25%, at least 30% of the extracellular matrix. Typically the extracellular matrix is grown until it achieves a thickness of at least 50 microns, at least 100 microns, at least 150 microns, at least 200 microns, at least 250 microns, at least 300 microns, at least 400 microns, or at least 500 microns. Diameter of the conduits may be controlled during manufacturing. Typically these may have an internal diameter of at least 10, at least 15, at least 20, at least 25, at least 30, at least 35, 40, at least 45, at least 50 mm.

Under some circumstances, it may be desirable to have live cells on or within the conduit. Such cells may be seeded upon the conduit and either grown in culture or grown in situ. The cells may be seeded in situ as well, by endogenous cells of the recipient which migrate and establish themselves on the artificial prosthesis. The cells may be derived from the patient or from another source. The cells may be useful for mimicking and recreating natural conditions in the host. Alternatively the cells may be used as in situ factories to produce a product that is desirable, such as a growth hormone, chemokine, blood factor, and the like. Suitable cells for seeding on an airway conduit include without limitation tracheal cells such as epithelial cells, cartilage cells, endothelial cells, smooth muscle cells, and fibroblasts.

A stent for use in an airway prosthesis may be made of metal, a polymer, or other natural or artificial biocompatible substance. The stent may be non-degradable, or may be degradable. These stents typically have a perforated structure, which permits attachment of inner and outer layers of substrate, for example, mesh or fabric. In some embodiments, the stent is provided with mesh only on the outer surface of the stent, thereby allowing cells to grow and extracellular matrix on the outside and then subsequently completely envelope the struts of the stent. In other embodiments, the mesh is applied only to the inside surface of stent, which after cell seeding also allows the cells to envelope both the mesh and the struts of the stent with both cells and extracellular matrix. One suitable mesh which can be used as a substrate for cell growth is made of polyglycolic acid. Typically, during culturing polyglycolic acid mesh degrades spontaneously, and fragments of it are washed away in the culture medium or are phagocytosed by the cultured cells and degraded. Some fragments may remain. Other biodegradable on non-degradable substrates can be used as are known in the art, such as polylactic acid, polycaprolactone, polyanhydrides, polyethylene glycol, as well as other biocompatible polymeric substances. Other biocompatible substrates include collagen, gelatin, elastin, cellulose, alginate, and other substances which support the growth of cells in culture. Substrates may be in a mesh format, or may take the form of a gel or a sponge.

While the conduits are described as tubular, they may also contain one or more branches, so that the conduit is in the shape of for example, a Y, X, T, or F. Conduits with such branches are considered tubular, as well. The conduits described may be implanted to replace, line, reinforce, or by-pass an existing physiological or implanted conduit.

Conduits which are made by growing cells on a tubular stent may have an additional advantage over conduits formed using rolled sheets inside and outside of a stent. The conduits made by growing cells may have the extracellular matrix rotationally fixed with respect to the stent. The inner and outer surfaces of extracellular matrix may additionally be rotationally fixed with respect to one another. Being so fixed, slippage and leakage is minimized. The two surfaces may be so fixed by, for example, interlacing the substrates upon which the cells secreting the extracellular matrix are grown. The cells and extracellular matrix may, for example, envelope or bridge the stent struts, and may completely incorporate the stent material.

Conduits that are grown by culturing cells on a substrate that encases a tubular stent, either on the inside or the outside or on both sides, have the advantage of being comprised of a single tissue that envelopes and encases the stent material. The resulting material is a true tissue-stent composite material. This configuration has many functional advantages over earlier systems that involve rolling a sheet of tissue around the inside or outside of a stent. For example, in situations where tissue is rolled around the stent, it can occur that the sheets of tissue do not fuse with each other, or do not fuse with the stent material. This lack of fusion of tissue sheets results in a construct in which pieces of tissue and stent material can slip relative to one another, resulting in a conduit which is structurally unstable Iii contrast, by culturing cells on a scaffold which fully encases the stent material, the resulting conduit is comprised of a single piece of tissue-stent composite material, and contains no sheets of tissue which may move or slip relative to one another. Such conduits are then more highly suited to various applications wherein the conduit must be liquid-tight or air-tight. In addition, such conduits are more highly suited to serving as replacements for native tubular tissues, such as trachea, bronchus, intestine, esophagus, ureter, urinary conduit, or other tubular tissues which must function to contain liquid or air or both. In contrast, stents that are wrapped with sheets of exogenous tissue may be poorly suited for these applications, since the slippage of tissues and stent material can cause leakage of air or fluid. In addition, a single tissue-stent composite material displays superior handling properties for surgical implantation, in contrast to wrapped tissue sheets which can slide and become detached from the stent material. In addition, a single tissue-stent composite material will withstand physiological stresses following implantation, such as pressurization, shear forces, fluid flow, and the like, while a stent encased in tissue sheets may delaminate and lose structural integrity upon exposure to physiological forces in the body.

Decellularization of the conduit may involve the killing and/or removal of cells from a scaffold or substrate. Any means known in the art may be used, including but not limited to the use of agitation and the use of detergents. The decellularization process must be balanced between the limits of being sufficiently harsh to kill or dislodge the cells and sufficiently gentle to maintain the extracellular matrix structure intact. Substantially acellular extracellular matrix remains after the decellularization process. The prosthesis contains less than 50%, less than 75%, less than 80%, less than 85%, less than 90%, or less than 95% of the cells viable, as assessed by trypan blue staining, BrdU nucleotide incorporation, TUNEL staining, or protein synthesis.

Prostheses or conduits may be stored prior to implantation in a recipient mammal. The storage may occur before or after decellularization has occurred. Storage may be at various temperatures, but typically will be at or below 4 deg C., 0 deg C., −20 deg C., −40 deg C., or −60 deg C. Storage may be for at least hours, at least days, at least weeks, at least months or at least years. In addition, conduits may be stored at room temperature, at or below 20 deg C., 25 deg C., 30 deg C., 35 deg C., or 40 deg C. In general, it is not desirable to store the conduits at temperatures above 40 deg C.

Trachea serves the function of conducting humidified air from the outside into the lungs. To serve this purpose, a trachea replacement tissue must be able to withstand compressive pressures and negative intra-luminal pressure. This is because, every time we take an inhaled breath, we exert a negative pressure on the tracheal lumen. Thus, to remain patent during inspiration, it is necessary for a trachea to be invested with some sort of "stenting" function that prevents collapse. In the native trachea, this function is sub-served by rings of cartilage tissue that are embedded in the wall of the trachea. In the engineered trachea (conduit), this stenting function is served by a metal (or other material) stent that is physically embedded inside an engineered tissue.

Another key aspect of functional tracheal tissue is the ability to remain air- and liquid-tight. This is because air that we inhale is filled with particles and micro-organisms. If micro-organism-containing air were allowed to penetrate into the mediastinum of the patient, then this would result in a mediastinal infection that would cause excessive morbidity/mortality. Hence, any replacement trachea should be "tight" to liquid and air in order to be function, From the data shown below, it is apparent that the engineered trachea is water-tight. In addition, animal implantation studies of engineered trachea show that the trachea maintains patency during respiration, and does not leak either liquid or air, does not develop infection or perforation, and adequately serves as a conduit to conduct air to the lungs of the animal.

Another function of trachea is to produce mucous which protects the wall of the trachea from invading organisms and excessive dehydration. This mucous is generally produced by mucous-producing cells on the lumen of the trachea. Our current engineered trachea consists solely of decellularized matrix that envelopes a metal stent. After implantation, the engineered trachea re-populates with native tracheal epithelial cells from the recipient, as shown in the drawings. By becoming densely invested with native cells of the trachea, the implanted and initially acellular trachea becomes more physiologically functional. Alternatively, it may be possible to "pre-coat" the engineered trachea with autologous epithelial cells prior to implantation.

One advantage of the tissue-stent composite trachea is that the stent material is encased in tissue and is therefore shielded from particles and micro-organisms that are inhaled during respiration. This, in turn, results in resistance to infection of the stent material, or colonization with bacteria, fungi, or other inhaled micro-organisms. By completely encasing the stent material, predisposition to stent infection is minimized and hence function is enhanced.

The engineered trachea may be comprised of a stent (which can be made of metal, although it could be made of any biocompatible stenting material, such as a degradable or non-degradable polymer), around which is cultured a layer of vascular smooth muscle cells. To culture the cells on the stent, one or two layers of degradable polymer scaffold made of, for example, polyglycolic acid (PGA) mesh can be wrapped around the stent—one on the outside of the stent, one on the inside, or just one layer on one side of the stent, depending upon the usage and application. The layers of PGA mesh scaffold can then be interwoven to produce an encasement of the metal stent within two layers of PGA mesh. Alternatively, the stent can be manufactured so as to contain the mesh scaffold and the stent-scaffold material is produced as a single, composite piece. The sterilized stent-mesh composite can then be seeded with vascular smooth muscle cells. Airway smooth muscle is an important component of all large airways, including human trachea. The cells may be seeded onto the PGA mesh scaffold and cultured for 6-10 weeks in specialized growth media within a bioreactor. During this time, the smooth muscle cells can proliferate on the PGA mesh and secrete extracellular matrix, composed mainly of collagen but also containing other substances such as glycosaminoglycans, fibronectin, vitronectin, elastin, and other extracellular matrix molecules. At the conclusion of culture, the metal stent is then encased in engineered tissue comprised of smooth muscle cells, extracellular matrix, and PGA polymer fragments. The tissue can then be decellularized, to produce a substantially acellular, engineered trachea that is non-living and can be stored for several months in buffer solution. This structure should be non-immunogenic when implanted into any allogeneic (i.e., same species) recipient as the source of the smooth muscle cells.

Esophagus has several key functions in the body. First and most importantly, it must provide an air-tight and water-tight conduit that prevents the leakage of food into the surrounding mediastinum. Since all of the food and drink that we consume is contaminated with bacteria, it is essential that the esophagus retain all food material and prevent it from entering the chest/mediastinum, where it would cause infection with significant attendant morbidity/mortality. Additionally, it may impermeable to gas.

A second key function of the esophagus is to provide peristalsis, or rhythmic contractility, to force food from the upper esophagus into the stomach. To perform this function, the esophagus may be comprised mainly of intestinal smooth muscle that has rhythmic contractile capability. Other cells which may populate the artificial esophagus include such esophageal cells as epithelial cells, endothelial cells, smooth muscle cells, and fibroblasts. To maintain adequate tensile strength and prevent tearing, the esophagus also may have significant collagenous extracellular matrix. An esophagus will typically have a suture retention of greater than 100 grains, greater than 125 grams, greater than 150 grams, greater than 175 grams, greater than 200 grams, or greater than 225 grams. Its rupture strength may be greater than 500 mm Hg, greater than 750 mm Hg, greater than 1000 mm Hg, greater than 1250 mm Hg, greater than 1500 mm Hg, or greater than 2000 mm Hg. Unlike the tracheal prosthesis, the esophagus may not require any "stenting function" to maintain patency.

Our tissue engineered esophagus consists of an engineered tissue that is made from vascular smooth muscle cells that are cultured on a degradable polymer scaffold made of PGA. After 6-10 weeks of culture, the engineered tissue is decellularized, to produce a substantially acellular engineered esophagus that can be stored on the shelf for months at a time.

Urinary conduits may be transplanted into a recipient, such as a human patient, connecting one or both ureters of the patient and draining through a stoma in the skin, or replacing a segment of ureter or urethra. A urinary conduit will typically have a suture retention of greater than 100 grams, greater than 125 grams, greater than 150 grams, greater than 175 grams, greater than 200 grams, or greater than 22.5 grams. Its rupture strength may be greater than 500 mm Hg, greater than 750 mm Hg, greater than 1000 mm Hg, greater than 1250 mm Hg, greater than 1500 mm Hg, or greater than 2000 mm Hg. After implanting, a urinary conduit may be populated with endogenous cells such as urinary epithelial cells, endothelial cells, smooth muscle cells myofibroblasts, telocytes, or dermal epithelial cells (e.g., squamous epithelial cells) or keratinocytes, and fibroblasts. If desired, cells can be seeded prior to implanting. In some embodiments, a urinary conduit contains no stent, and in others, a stent is preferred. Urinary conduits are typically between 6 and 25 mm, often greater than 10 mm in diameter.

Some of the data described below with respect to both trachea and esophagus employed tissues produced from canine (dog) cells. Hence, the matrix shown in some data is canine matrix. In addition, engineered trachea, esophagus, or urinary conduit may be made by culturing human cells on a substrate, that optionally is also encasing a stent. In these cases, the final conduit contains human extracellular matrix. However, engineered airway, urinary conduit, and esophagus can be made using any mammalian or primate vascular smooth muscle cells, including human vascular smooth muscle cells. Such primates or mammals include, without limitation, pig, horse, donkey, cat, mouse, rat, cow, sheep, baboon, gibbon, and goat. Additionally, recipients of the prostheses can be without limitation mammals including, human, dog, pig, horse, donkey, cat, mouse, rat, cow, sheep, baboon, gibbon, and goat.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

Example 1

Tracheal PGA Scaffold Preparation

A poly(glycolic) acid (PGA) sheet is cut into 5.4 cm×8.5 cm and 5.2 cm×8.5 cm pieces. 5.2 cm×8.5 cm PGA mesh is rolled into a tube and inserted inside a bare-metal stent (1.7×8.5 cm). 5.4 cm×8.5 cm PGA mesh is then sewn around the bare-metal stent using the absorbable PGA suture, sandwiching the stent between the two layers of PGA mesh. A crochet needle is applied carefully throughout the PGA/stent construct to interlace the two PGA layers together. A non-absorbable suture is sewn through both ends of PGA/stent construct to suspend the construct inside a specially designed bioreactor for trachea reconstruction. The construct is then dipped into 1M NaOH solution for 2 minutes to treat the surface of the PGA mesh followed by three rinsing in distilled water. The PGA/stent construct is then assembled in the bioreactor as shown in FIG. 1.

Example 2

Smooth Muscle Cells (SMC) Seeding and Tracheal Culture Maintenance

Figure 2:
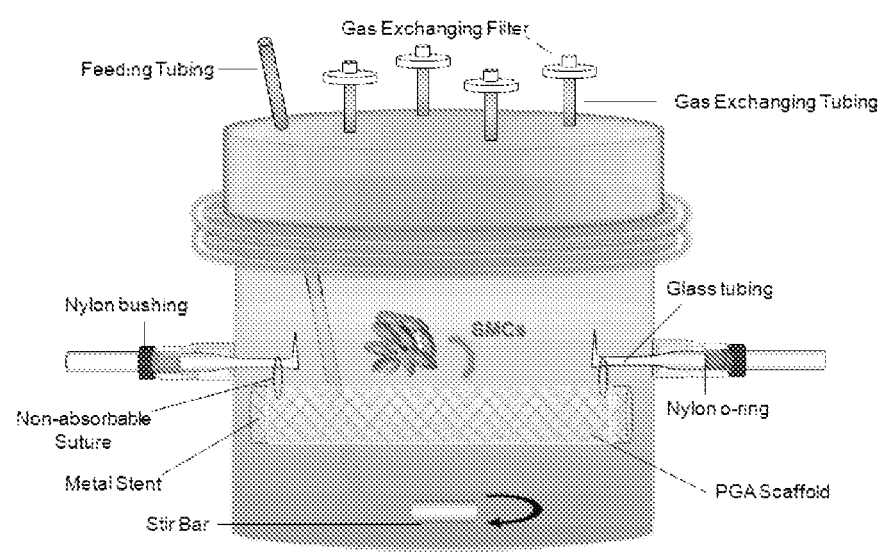
FIG. 2: Seeding of smooth muscle cells (SMCs) onto PGA mesh encasing metal stent in the bioreactor.
Figures 3A, 3B:
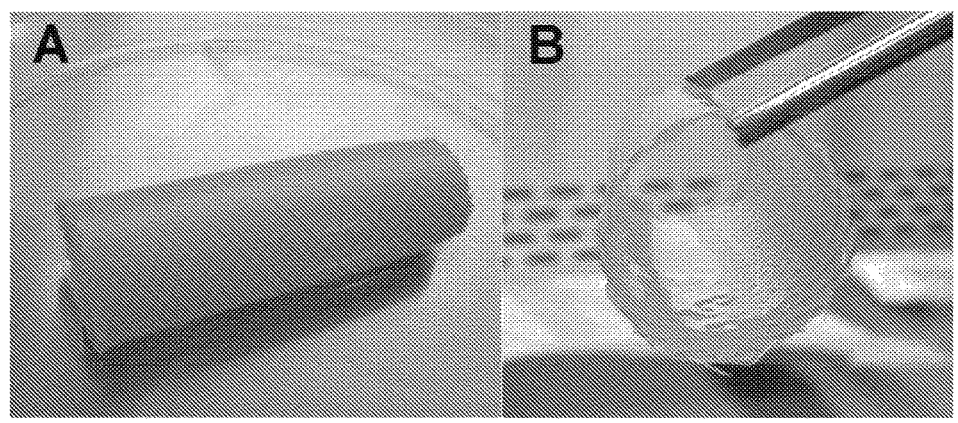
FIG. 3A-3B: Gross photos of engineered trachea. Smooth muscle cells cultured on PGA mesh surrounding a metal stent. After 8 weeks of culture, cells are removed by decellularization, leaving behind the engineered extracellular matrix encasing the metal stent. This engineered trachea is 1.6 cm in diameter and approximately 8 cm in length.

Primary SMCs were isolated from dog aortas and expanded in T-75s in 20% fetal bovine serum (FBS) low glucose Dulbecco's Modified Eagle's Medium. 120 million SMCs of P2 and P3 were re-suspended in 7 ml of medium and seeded onto the PGA/Stent construct inside the bioreactor, as shown in FIG. 2. The construct was cultured inside the bioreactor statically for 12 weeks in 1.3 L of low glucose Dulbecco's Modified Eagle's Medium with 20% FBS, basic fibroblast growth factor (10 ng/ml), platelet derived growth factor (10 ng ml), L-ascorbic acid, copper sulfate, HEPES, L-proline, L-alanine, L-glycine, and Penicillin G (FIG. 2), Medium was changed 1.5 times per week and ascorbic acid was supplemented three times per week.

Example 3

Decellularization of Engineered Trachea

Engineered trachea (6 cm in length) was first incubated in 250 mL CHAPS buffer (8 mM CHAPS, 1M NaCl, and 25 mM EDTA in PBS) for 45 minutes at 37 C.° under high-speed agitation, followed by thorough sterile PBS rinsing. The engineered trachea was further treated with 250 mL sodium dodecyl sulfate (SDS) buffer (1.8 mM SDS, 1M NaCl, and 25 mM EDTA in PBS) for 45 minutes at 37 C.° with high-speed agitation. The engineered trachea then underwent 2 days of washing in PBS to completely remove the residual detergent. All decellularization steps were performed under sterile conditions. The decellularized engineered trachea was stored in sterile PBS containing penicillin 100 U/mL and streptomycin 100 mg/mL at 4 C.°.

Example 4

Figure 6:
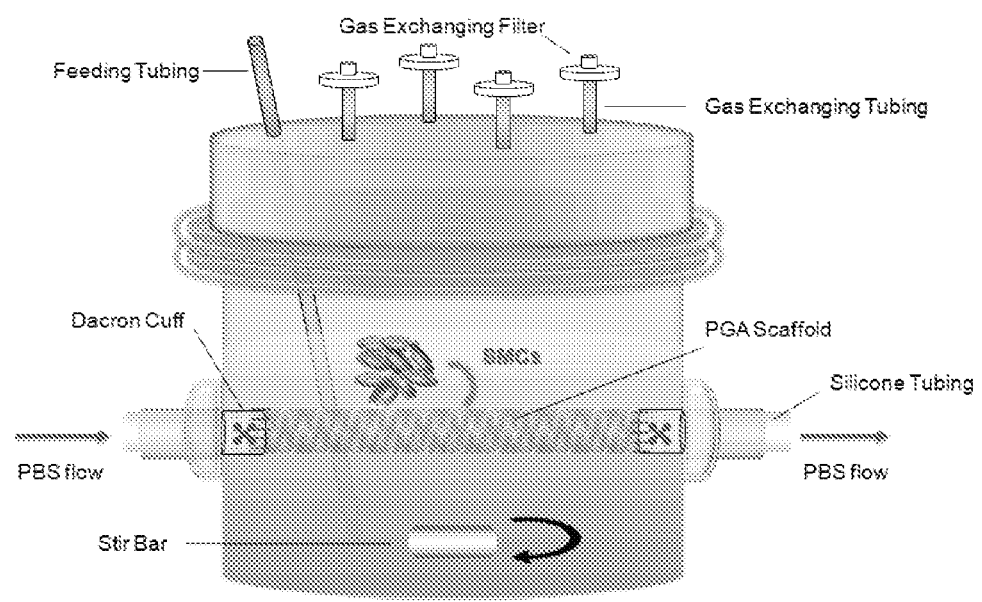
FIG. 6: Schematic of culture of engineered esophagus in bioreactor.
Figure 7:
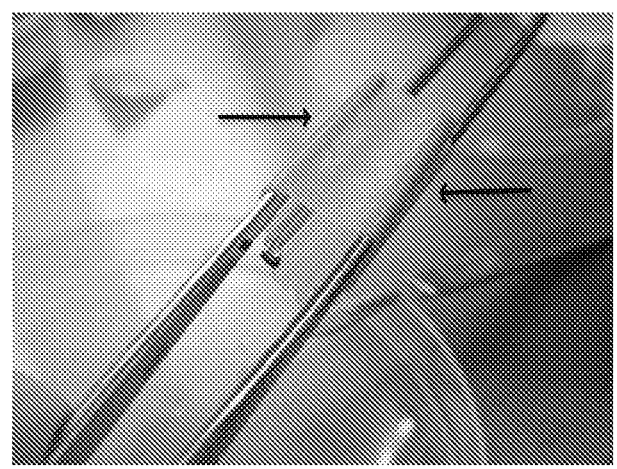
FIG. 7: Engineered acellular esophagus held with forceps. Segment of engineered esophagus is 1.5 cm in diameter by 5 cm in length. It is strong enough to hold retraction by two sets of forceps, shown. Esophagus is shown by arrows on either side.
Figures 8A, 8B, 8C:
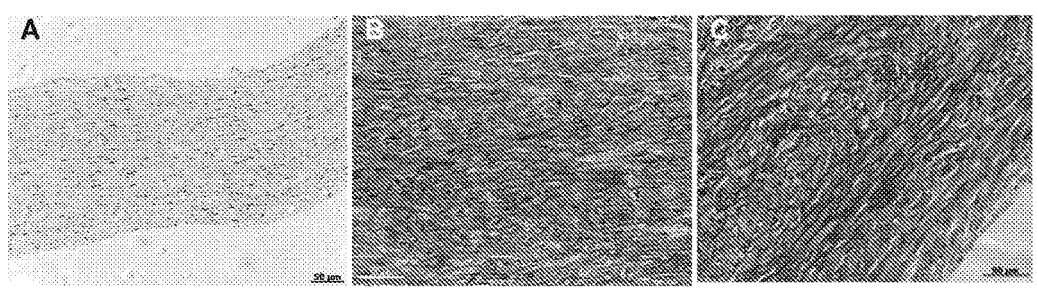
FIG. 8A-8C: Histologies of engineered esophagus.
Figure 9:
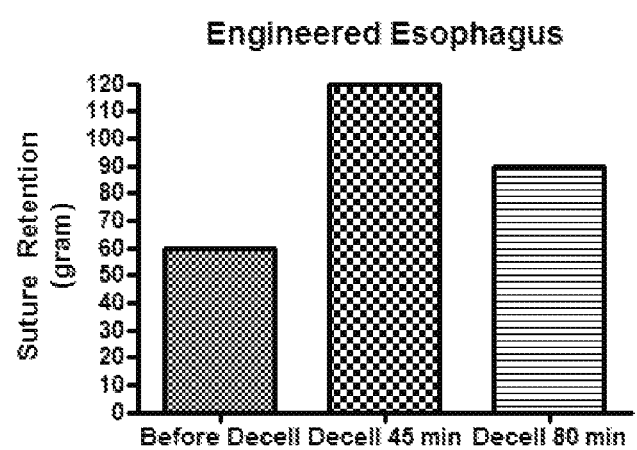
FIG. 9: Suture retention strength of engineered esophagus. Suture retention in grams is shown before decellularization, and after decellularization regimens lasting either 0.45 or 80 minutes. After 0.45 minutes of decellularization, suture retention strength is greater than 100 grams. This is indicative of an implantable engineered tissue (Dahl, et al, Science Translational Medicine 3:68pc2, 2011).
Figure 10:
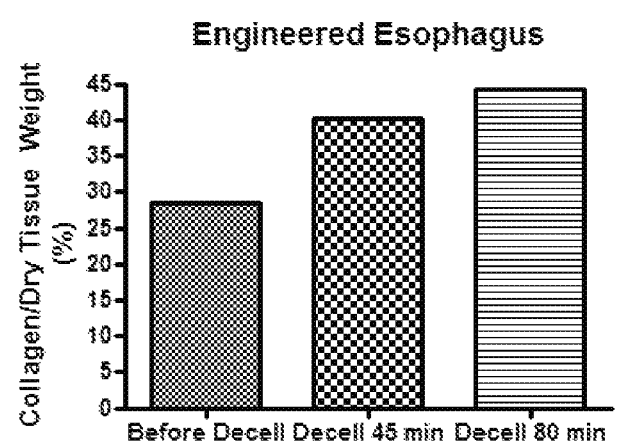
FIG. 10: Collagen content of engineered esophagus. Hydroxyproline content of engineered esophagus before decellularization, and after 45 and 80 minutes of decellularization. Progressive decellularization removes more cellular material, thereby increasing the percentage of collagen remaining in the tissue as a fraction of dry weight.

Esophagus PGA Scaffold Preparation 6.5 cm×10 cm PGA sheet is sewn into a cylindrical construct with absorbable PGA suture around a compliant silicone tubing (inner diameter=2 cm) with a suture line that is axially aligned to the PGA cylindrical scaffold. Dacron cuffs are then sewn onto the ends of the PGA tubular construct, one on each end. The construct is dipped into 1M NaOH solution for 2 minutes to treat the surface of the PGA mesh followed by three subsequent wash in distilled water. The PGA scaffold and silicone tubing are assembled inside a bioreactor as shown in FIG. 6.

Example 5

Figure 4:
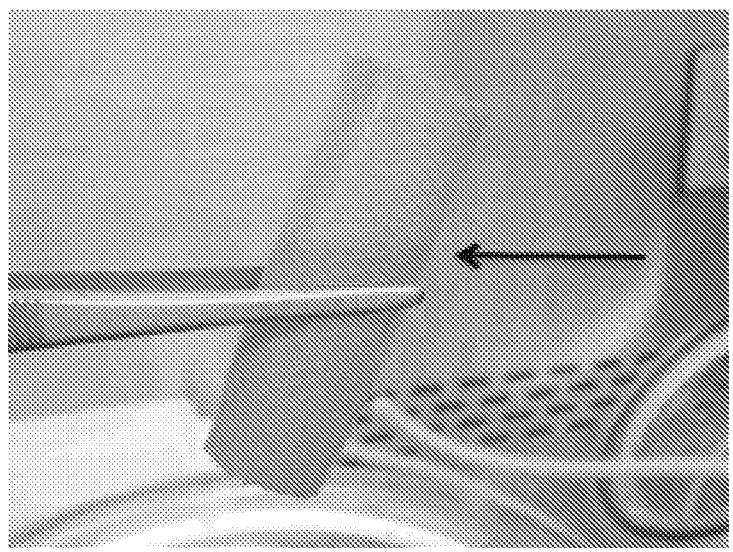
FIG. 4: Gross photo of engineered trachea, showing water-tight tissue. Engineered trachea is 1.6 cm in diameter and 8 cm in length. The engineered trachea, consisting of decellularized tissue encasing a metal stent, is filled with colored liquid and held aloft. The acellular tissue, which envelopes the walls and end of the stent, is sufficiently robust to hold liquid, as the visible level of red liquid inside the trachea, demonstrates (arrow).
Figure 5:
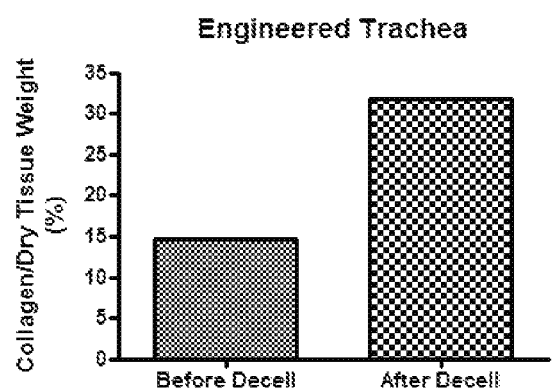
FIG. 5: Collagen content of engineered trachea tissues: Biochemical assay for hydroxyproline shows collagen content as a fraction of dry tissue weight, before and after decellularization. Increase in collagen as a fraction of dry weight after decellularization indicates that cellular material is removed, while collagenous exxtracellular matrix remains.

Smooth Muscle Cells (SMC) Seeding and Pulsatile Flow System for Engineered Esophagus million dog SMCs of P2 and P3 were re-suspended in 5 ml of medium and seeded onto the PGA construct inside the bioreactor. The seeded construct was cultured inside the bioreactor connecting to a peristaltic pump, which creates cyclic radial strain of 3.0% at 1.5 Hz. The engineered esophagus was cultured in the pulsatile culture for 10 weeks and maintained with 1.31, of low glucose Dulbecco's Modified Eagle's Medium with 20% FBS, basic fibroblast growth factor (10 ng/ml), platelet derived growth factor (10 ng L-ascorbic acid, copper sulfate, HERPES, L-proline, L-alanine, L-glycine, and Penicillin G (FIG. 4). Half of medium volume was changed 1.5 times per week and ascorbic acid was supplemented three times per week.

Example 6

Decellularization of Engineered Esophagus

The engineered esophagus was cut into two 3 cm-length pieces and were first incubated in 250 mL CHAPS buffer (8 mM CHAPS, 1M NaCl, and 25 mM EDTA in PBS) for either 45 or 80 minutes at 37 C.° under high-speed agitation, followed by thorough sterile PBS rinsing. The engineered esophagus pieces were further treated with 250 mL, sodium dodecyl sulfate (SDS) buffer (1.8 mM SDS, 1M NaCl, and 25 mM EDTA in PBS) for 45 or 80 minutes at 37 C.° with high-speed agitation. The engineered esophagus pieces were then washed with PBS for two days to completely remove the residual detergent. All decellularization steps were conducted under sterile conditions. The decellularized engineered esophagus pieces were stored in sterile PBS containing penicillin 100 U/mL, and streptomycin 100 mg/mL at 4 C.°.

Example 7

Suture Retention of Engineered Esophagus

Weights are hanged from a suture line threaded onto one side of engineered esophagus, 2.5 to 3 mm away from the edge. Weights are incrementally added to the suture until the suture is torn from the tissue. The total weight at which the tissue is torn is recorded in units of gram.

Example 8

Engineered Trachea for Implantation into Rat Recipient and Results of Implantations A 4-mm diameter metal stent is encased with PGA scaffolding, sterilized, and seeded with human vascular smooth muscle cells. The stent-scaffold-cell structure is cultured within a bioreactor for a period of 6-10 weeks in the presence of a nutrient culture medium. $2 \times 10^6$ P2 human smooth muscle cells (SMCs) are seeded onto the scaffold constructs (polygycolic acid mesh wrapped around a 4-mm diameter nitinol stent) with 4 mm diameter and 8 mm length. The tracheas were statically suspended on silicone tubing and cultured inside the bioreactor for 10 weeks. The bioreactor medium was composed of DMEM (high glucose), bFGF (5 ng/ml), EGF (0.5 ng/ml), lactic acid (0.5 g/L), insulin (0.13 U/ml), Pen G 100 U/ml, Proline/Glycine/Alanine solution, $CuSO_4$ (3 ng/ml), and vitamin C (50 ng/ml). TE tracheae were cultured in 400 ml of medium at all times and only half of the medium was replaced during every medium change. The bioreactor medium was changed 1.5-2 times per week and vitamin C was supplemented to the culture 3 times per week. Lactic acid was freshly added to the medium once a week. Tracheas were cultured in 20% human serum for the first 4 weeks. From the $5^{th}$ week on, tracheas were grown with 10% human serum.

After culture, the conduit is decellularized and stored under sterile conditions in phosphate buffered saline at 4 deg C. After several weeks of storage, the conduit is implanted into a nude rat recipient. The chest of a 205 g nude rat was trimmed with a shaver. A 2.5 cm incision was made from the neck region with a pair of surgical scissor. Muscle and surrounding tissues were separated layer by layer until the trachea was exposed. A full circumferential segment of the trachea that constitutes two cartilaginous rings was removed. Due to release from tension, the gap expanded to approximately 1 cm (depending on the individual animals). 8 mm trachea was placed in between the gap and was anastomosed end-to-end to native trachea with at least 4 interrupted 6-0 Prolene sutures for each end. Finally, the muscle and surrounding tissues were sewn together with sutures layer by layer.

At explanation after either 2 or 6 weeks of implant, the engineered trachea becomes invested with host epithelial cells in the lumen of the airway. During the implant time, no animals were treated with antibiotics. The implanted trachea also becomes invested with other host cells including fibroblasts, and also becomes invested with host micro-vasculature both in the wall of the engineered trachea and in the lumen of the engineered trachea. The dense and rapid influx of microvasculature (seen as early as 2 weeks after implantation, by histological evaluation) aids in resistance to infection, since host leukocytes can easily gain access to the implanted tissue to fight any infecting organisms. Over the longer term, the engineered trachea may also become invested with cartilaginous cells of the native trachea, as well as smooth muscle cells that occupy the native tracheal wall and other airways. The implanted tracheas all resisted dilatation, rupture, and perforation, which could lead to device failure and to infection in the animal. In addition, the engineered implanted tracheas did not show any evidence of either immune rejection, or of bacterial or fungal infection, during the entirely of the implantation period. The implanted trachea may resist stenosis or scarring which limits air flow to the lungs.

Figure 17:
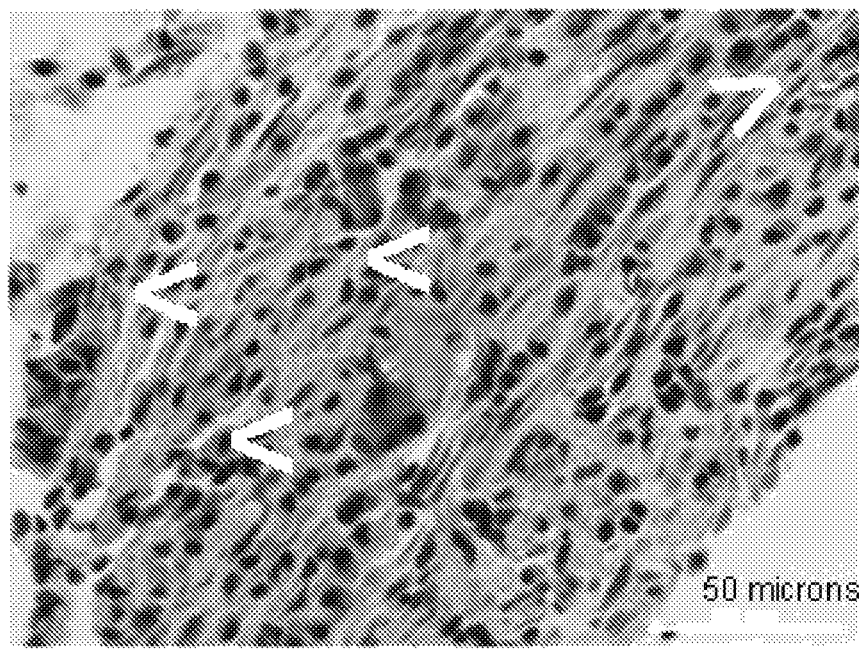
FIG. 17: H&E stain of tissue that has grown from host airway inside of the engineered trachea after 2 weeks of implantation. White arrowheads point out red blood cells in capillaries in the tissue ingrowth, indicating extensive microvascularization of ingrown tissue. Scale bar is 50 microns.
Figure 18:
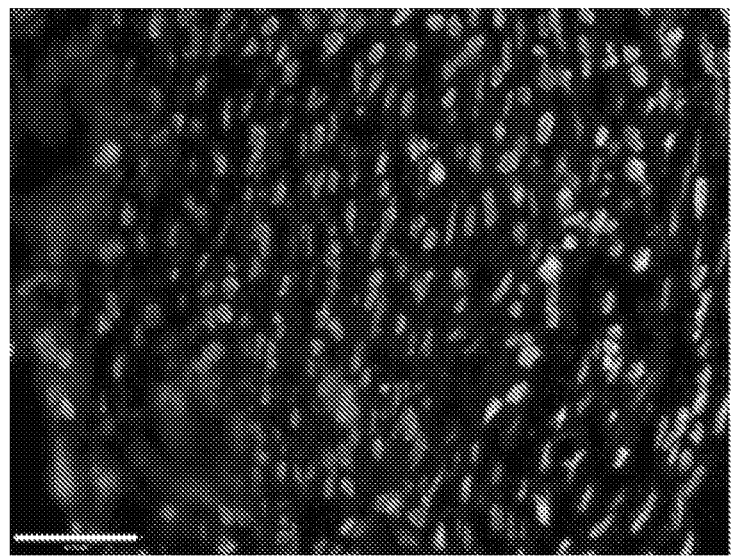
FIG. 18: Immunostain of tissue ingrown into lumen of engineered trachea after 2 weeks of implantation. Blue is DAPI nuclear stain, while red is immunostain for cytokeratn-14, a marker of tracheal epithelium. This image shows that many of the cells in the lumen of the engineered trachea were ingrown epithelium from the recipient, Scale bar 50 microns.

Engineered, decellularized human tracheas were explanted from rat recipients at two week and six weeks. After two weeks of implantation, robust tissue formation was observed in the lumen of the engineered tracheas, with evidence of extensive microvascularization. Also after two weeks, luminal tissue was immunostained and was strongly positive for cytokeratin-14, an epithelial marker. See FIGS. 17 and 18.

Figure 19:
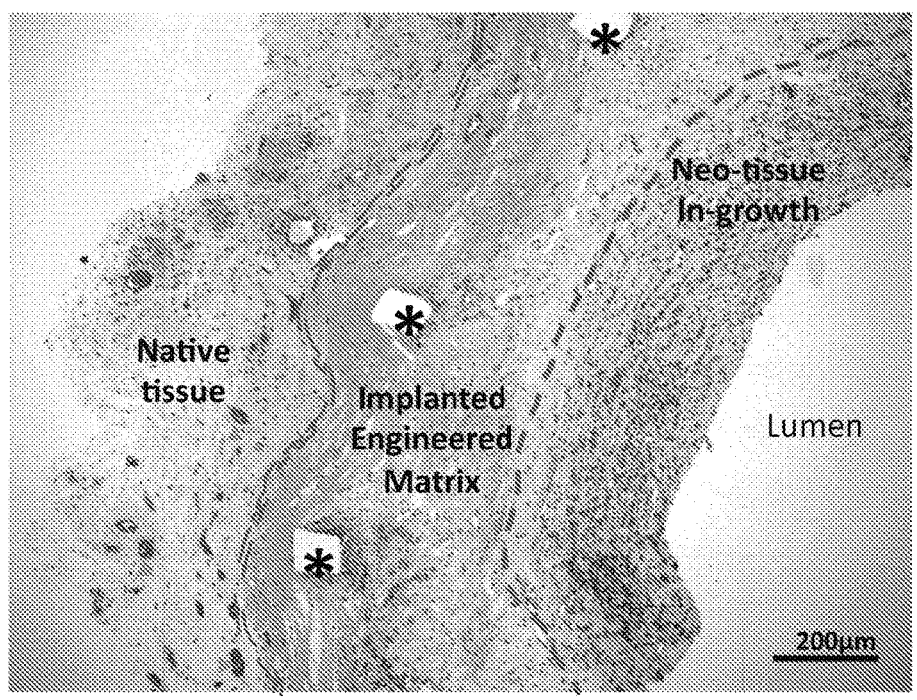
FIG. 19: Low-power H&E image of engineered, human decellularized trachea that was implanted into a nude rat for 6 weeks and then explanted. Surrounding native fibrous tissue is indicated. Locations of struts of nitinol stent, visible as square holes in the tissue, are indicated with asterisks (*). The implanted engineered matrix has some evidence of cellular infiltration after 6 weeks of implantation (nuclei visible in between struts, and near bottom of image). Neo-tissue in-growth in the lumen of the engineered trachea is visible. Scale bar 20 microns.
Figure 20A:
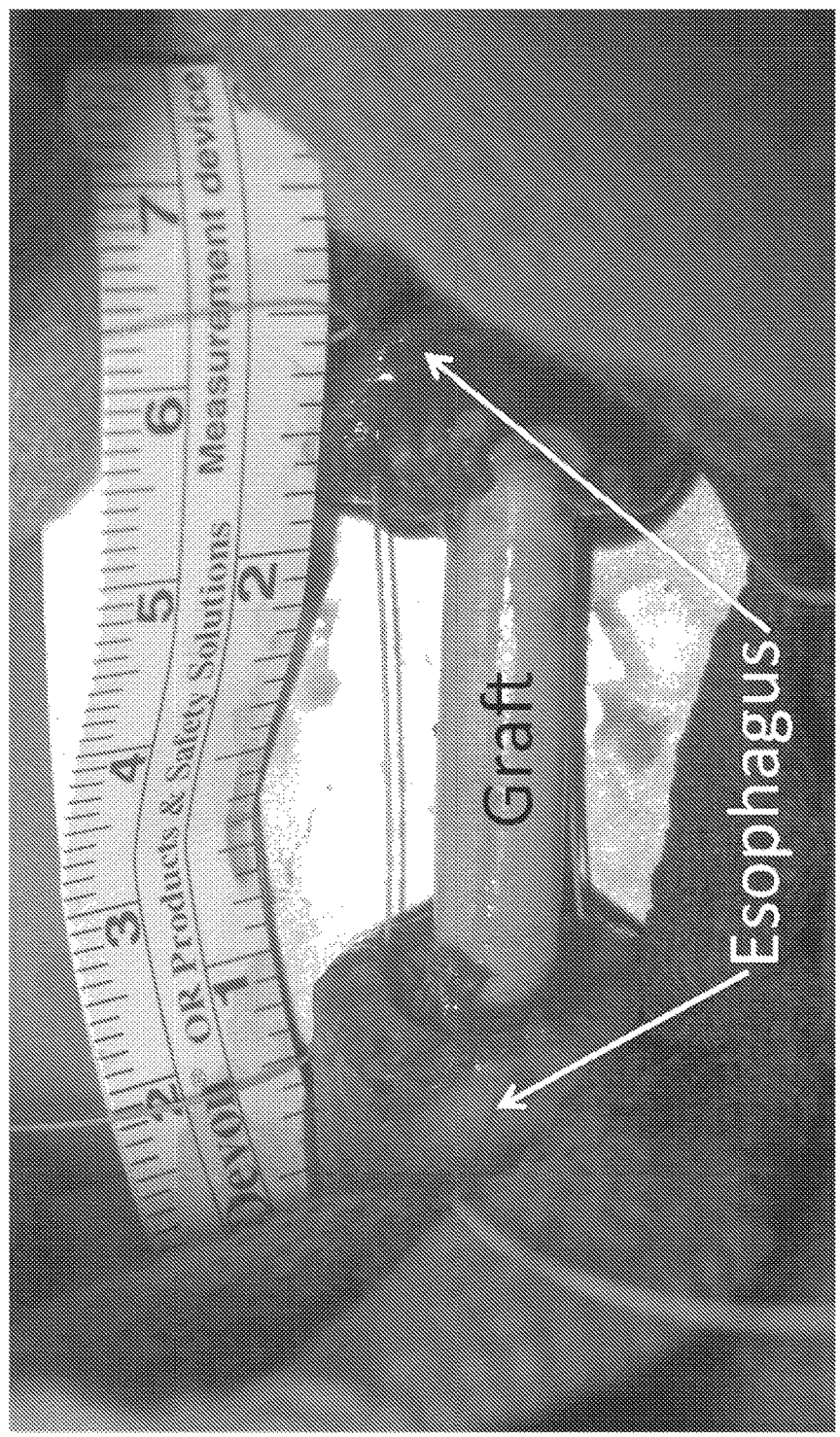
FIGS. 20A-20B: A graft was sewn into the esophagus of a pig to replace an excised segment of esophagus (FIGS. 20A-20B), This shows the potential for full-circumference replacement of esophagus.
Figure 20B:
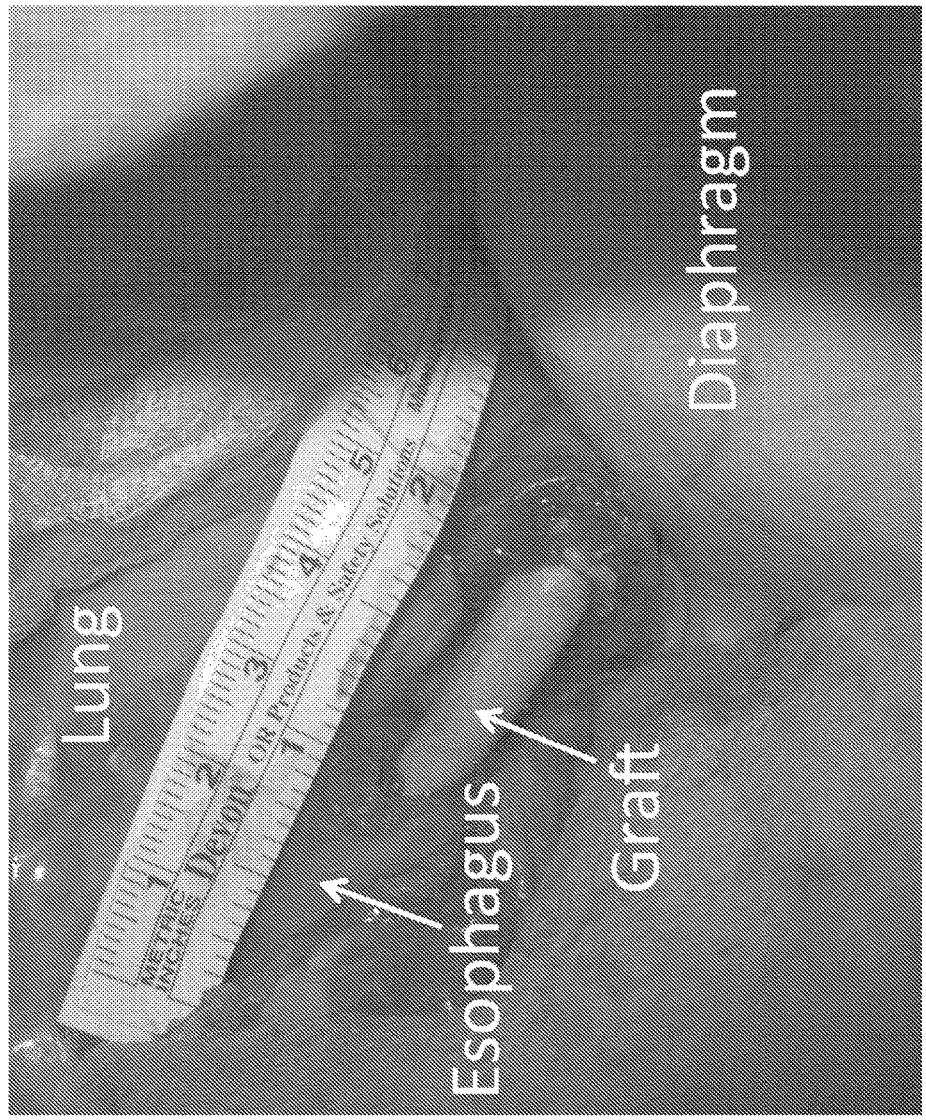
Figure 21:
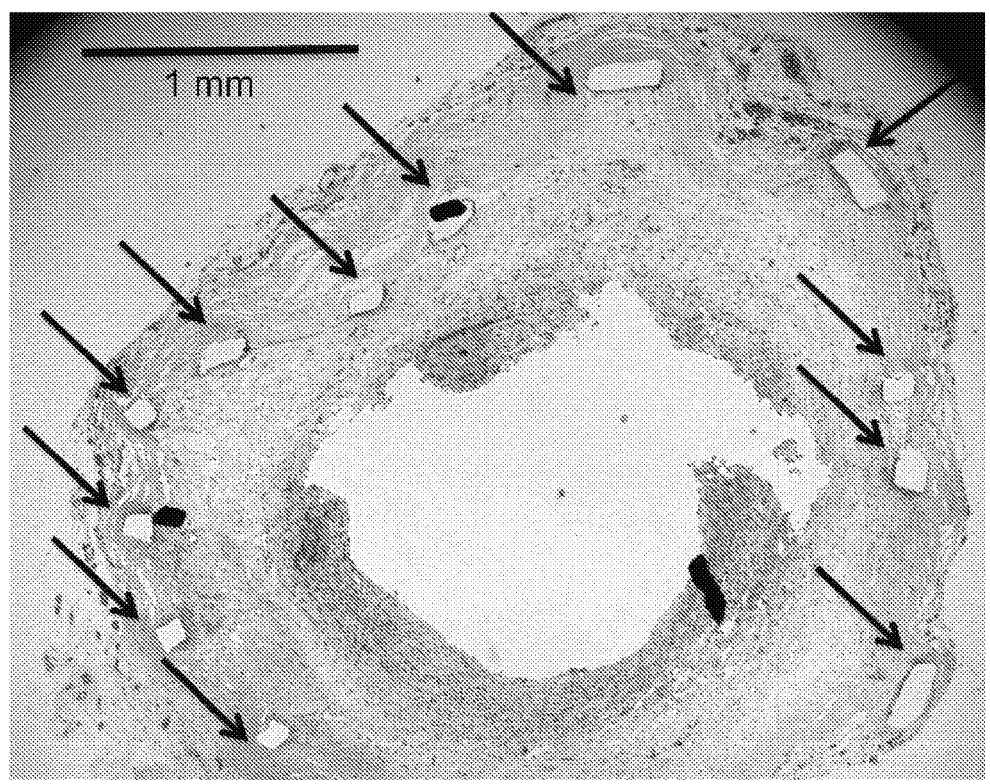
FIG. 21: H&E stain of engineered trachea that was implanted and then explanted after 6 weeks. Holes in tissue section that contained stent struts are indicated by black arrows. Clearly, struts of the stent are densely embedded into the extracellular matrix tissue (pink and orange in the image). An inner tissue layer of epithelium (purple nuclei) has also formed in the engineered trachea. Scale bar=1 mm.

After 6 weeks of implantation, engineered tracheas displayed good incorporation into host tissues, with formation of fibrous tissue surrounding the implanted engineered trachea, some evidence of residual decellularized human matrix, as well as ingrowth of luminal tissue. There was also some evidence of host cell infiltration into the previously acellular matrix of the tracheal implant. The implanted, engineered trachea was physically intact, without evidence of distension, perforation, or anastomotic breakdown. No evidence of excessive leukocyte infiltration or infection was observed in explanted specimens. See FIG. 19.

These results overall show that producing engineered, decellularized tracheas is feasible. Engineered tracheas can be sutured into recipient airways and can conduct air and allow the recipient to survive for long time periods. Engineered tracheas do not exhibit evidence of infection after implantation, and rapidly become invested with host cells and tissues and microvasculature after only a few weeks. Cells and tissue that infiltrates the engineered tracheas is highly vascular, and also contains cells that are native to the respiratory system (pulmonary epithelium). Engineered tracheas remain mechanically robust and do not suffer from mechanical failures such as perforation, dilatation, rupture, or anastomotic breakdown.

Example 9

Urinary Conduits

Based on methods pioneered by Dahl, Niklason, and colleagues [6-10], we have developed methods to grow tubular engineered tissues from banked human smooth muscle cells (SMC) that are seeded onto a biodegradable scaffold and cultured in bioreactors. No cells are harvested from the recipient for this process. After 10 weeks of culture, the engineered tissues are comprised of SMC and the extracellular matrix they have produced, which is primarily type I collagen. These tissues are then decellularized, creating an acellular tubular tissue that has excellent mechanical characteristics (rupture strengths >2,000 mm Hg) [10]. We have tested these tubular engineered tissues as arteriovenous grafts in a baboon model, and they have shown excellent function, biocompatibility, zero mechanical failures, and zero infection.

TABLE 1

|  | Suture Strength, g | Burst Press, mmHg |
| --- | --- | --- |
| 6-mm diameter conduit | 178 ± 11 (n = 37) | 3337 ± 343 (n = 10) |
| 6-mm conduit, stored 12 months in PBS buffer | 170 ± 22 (n = 9) | 2651 ± 329 (n = 5) |

We believe that the acellular engineered tissues will mitigate many of the complications that are associated with ileal conduits. Because our tissues are non-living and repopulate gradually with host cells, conduit ischemia and the associated mechanical failures will be extremely unlikely. Because our tissues do not actively absorb electrolytes, they should not cause a metabolic acidosis. Because our conduits do not foster the growth of commensal bacteria, they should not trigger recurrent urinary tract infections, And because they are available off-the-shelf, complications due to bowel resection will be avoided. Our acellular tubular engineered tissues have many favorable properties that may make them superior to segments of small intestine for urinary diversion. Since our urinal); conduit is pre-manufactured using banked cells and can be stored on the shelf, there is no need to resect a segment of intestine from the patient—surgery on the bowel is completely avoided. Since our conduit is non-living, there is essentially no risk of tissue ischemia after implantation. Rather, host cells gradually migrate into the acellular matrix, with formation of commensurate microvasculature. Since our conduit does not actively absorb its luminal contents, the risk of hyperchloremic metabolic acidosis is substantially reduced. And, since our conduit does not harbor intestinal flora, the risks of recurrent urinary tract infections should be markedly reduced, Hence, essentially all of the common complications associated with use of an ileal conduit could be reduced or Obviated by our acellular engineered tissues [11].

Figure 11:
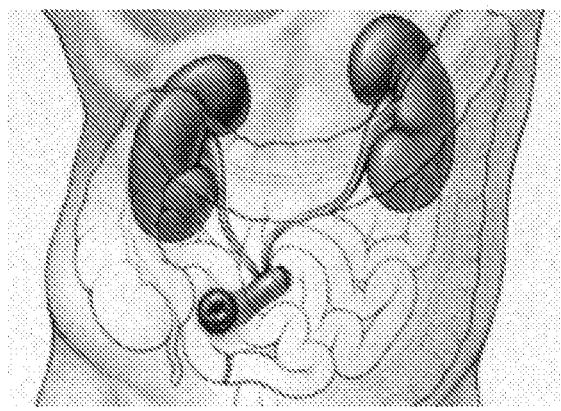
FIG. 11: Anatomy of ileal conduit implantation. Ureters are sewn to a segment of ileum, which is brought to the skin as a stoma.
Figures 12A, 12B, 12C:
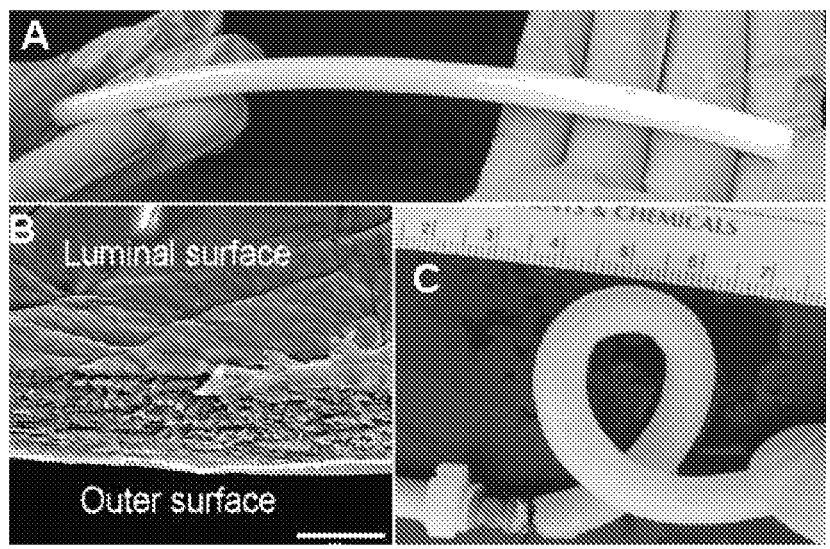
FIG. 12A-12C: Acellular engineered conduits.
Figures 13A, 13B, 13C:
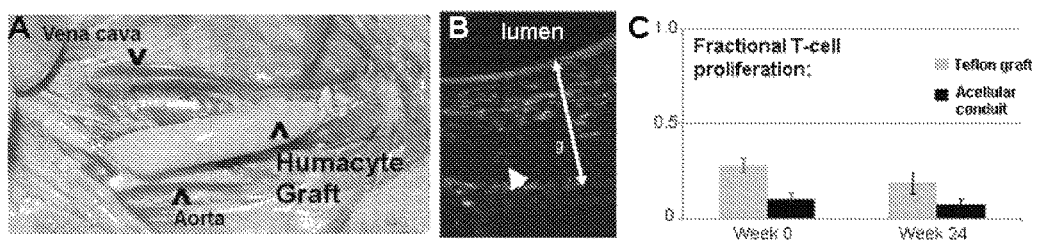
FIG. 13A-13C.
Figures 14A, 14B, 14C, 14D, 14E, 14F, 14G:
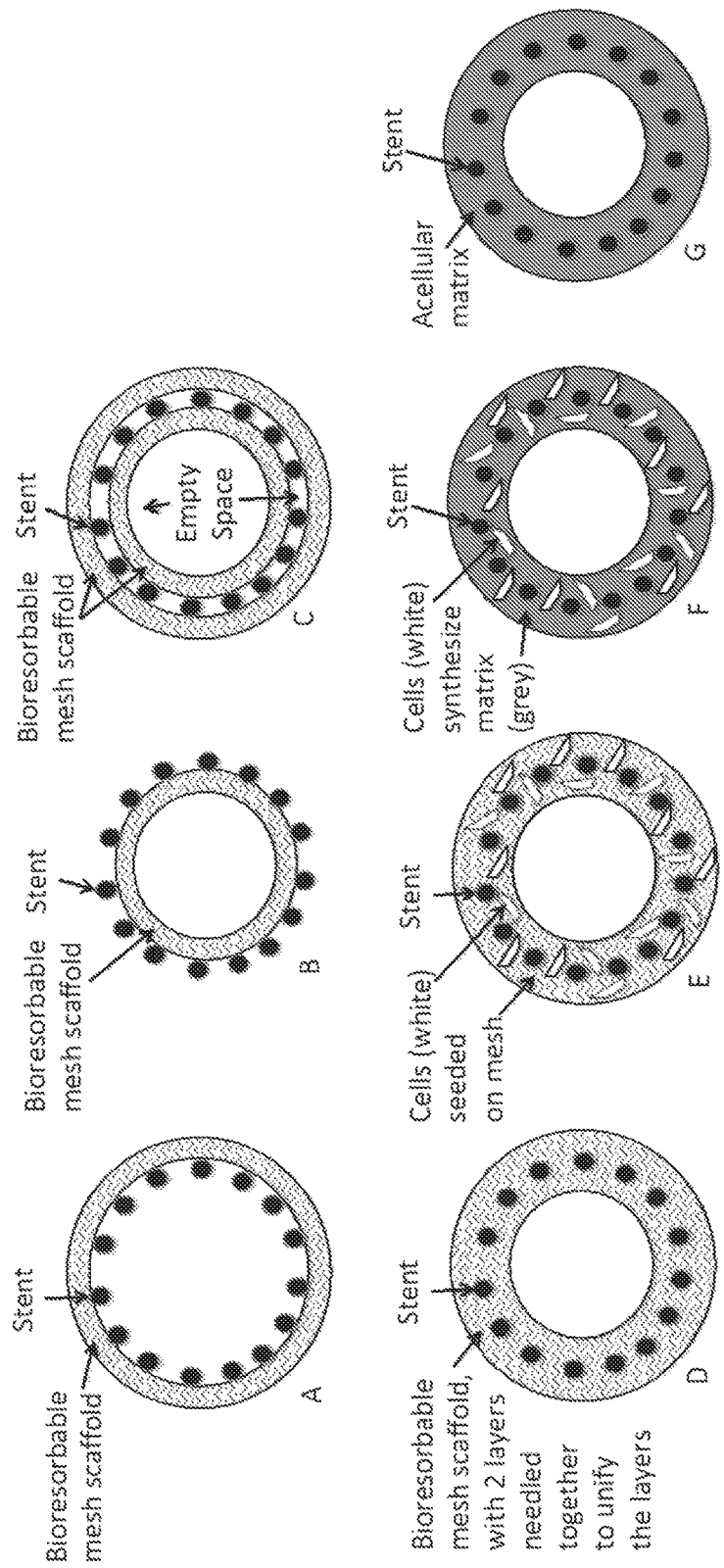
FIG. 14A-14G: Schematic drawings showing the growth and development of cells and matrix about a stent
Figure 15:
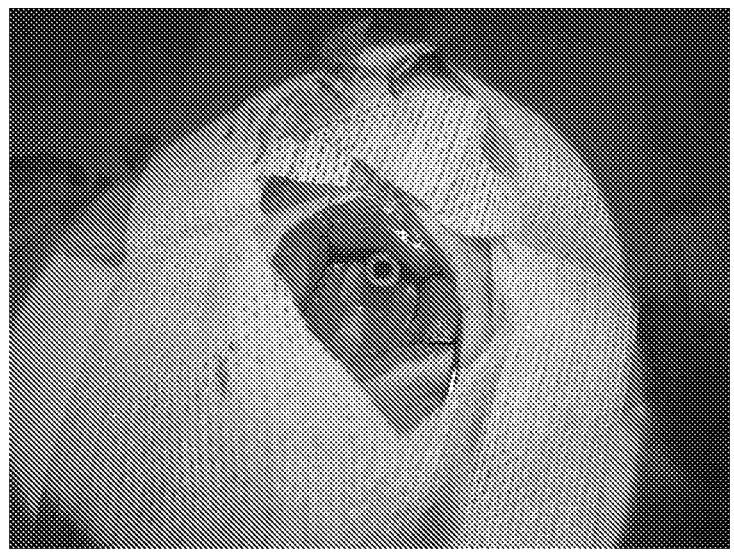
FIG. 15: Neck of rat open, with native trachea cut and two cartilagenous rings removed. Engineered trachea is anastomosed to proximal tracheal tissue, with distal end of engineered trachea extending upward.
Figure 16:
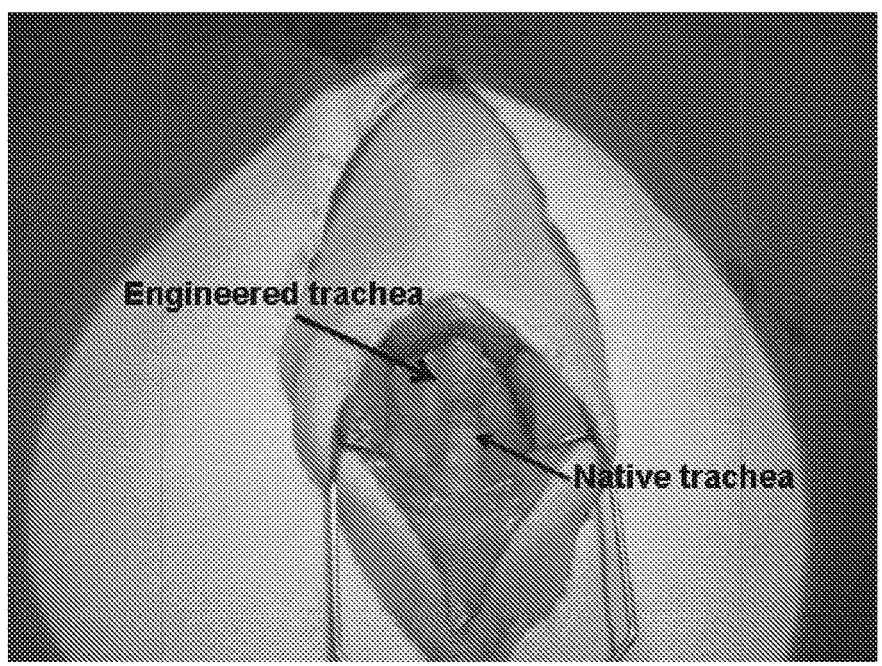
FIG. 16: Engineered human, decellularized trachea implanted into rat recipient. Native and engineered tracheal tissues are indicated in figure.

Approximately 10,000 cystectomies are performed annually in the US, with bladder cancer being the leading indication. In patients with T1 disease refractory to conservative measures and in patients with T2 tumors, surgical removal of the bladder with possible resection of associated pelvic organs remains the contemporary standard of care [12]. Other, less common reasons for cystectomy include neurogenic bladder (when it threatens renal function), severe radiation injury to the bladder, and intractable incontinence as well as chronic pelvic pain syndromes in females. All currently available surgical options for construction of urinary diversions involve the use of a segment of small or large intestine (FIG. 11). Though it is possible to build more complex, continent reservoirs, the majority of patients in North America undergoing cystectomy are reconstructed using the ilea conduit technique [13].

Shabsigh [14] reported that within 90 days of surgery, gastrointestinal complications occurred most commonly (29%), followed by infections (25%), wound related complications (15%), cardiac (11%), and genitourinary complications (11%). Electrolyte abnormalities, particularly metabolic acidosis, occur in 70% of patients, though often of unknown clinical significance. Severe electrolyte disturbances occur in 10% of patients with an ileal conduit [3, 5]. Osteomalacia can result from chronic acidosis with consequent release of calcium from bones. Acute pyelonephritis occurs in 10-17% of patients with colon and ileal conduits, and 4% of patients with ileal conduits die of sepsis [15], Cancer occurs in ileal conduits—anaplastic carcinoma and adenomatous polyps have been described. The reported rate for cancer in ileal conduits varies from 6-29% of all patients, though cancers can take decades to develop [5]. Early bowel complications typically consist of anastomotic leaks, enteric fistulas, bowel Obstruction, and prolonged ileus [11]. Bowel obstruction has been reported in as many as 5-10% of patients, with the majority responding well to conservative treatment while approximately 3% require surgery. Bowel anastomotic leak is a potentially devastating complication reported in 1-5% of patients, which can lead to abscess formation, peritonitis, and sepsis [5].

Example 10

Urinary Conduit

A urinary conduit is cultured using human smooth muscle cells that are cultured on a tube of PGA mesh scaffold in a bioreactor as described. After a culture period of 6-10 weeks, the resulting tubular tissue is decellularized, and then stored in phosphate buffered saline at 4 deg C. for a period of several months. Thereafter, a cynomolgus monkey (which is an old-world primate that is phylogenetically close to humans and is therefore unlikely to reject the human engineered tissue) is prepared for implantation of the urinary conduit. After induction of anesthesia, a laparotomy is performed and the ureters of both kidneys are isolated and excised from the bladder wall, which is oversewn. The ureters are anastomosed to the urinary conduit, the other end of which is anastomosed to the abdominal wall to allow urine to flow from the ureters, through the conduit, and outside the animal's body, After completion of the implantation, the abdomen is closed and the animal is recovered from anesthesia. Thereafter, the urinary conduit is seen to conduct urine to the outside of the body to a collecting bag. There is no evidence of leakage of urine into the abdomen or from the anastomoses with the abdominal wall or the ureters.

An implanted, engineered urinary conduit may become invested on the luminal surface with urinary epithelium. The implanted urinary conduit may become invested with fibroblasts in the wall of the conduit, may become invested with micro-vasculature which contributes to resistance to infection, and may become invested with smooth muscle cells similar to urinary bladder. The implanted, engineered urinary conduit may resist infection with skin flora and with organisms from the urinary tract. The implanted, engineered urinary conduit may resist scarring and constriction which would impede urine flow, it may resist dilatation which would cause pooling of urine in the conduit, it may resist kinking and obstruction which would impede urine flow, it may resist formation of intra-abdominal adhesions which can obstruct the conduit or intestinal tissues, and it may resist the creation of hyperchloremic metabolic acidosis in the host animal.

REFERENCES

The disclosure of each reference cited is expressly incorporated herein.
1. Healthcare Cost and Utilization Project, N.I.S., 2007.
2. Konety, B. R., Joyce, G. F., Wise, M., *Bladder and upper tract urothelial cancer.* Journal of Urology, 2007. 177: p. 1636-1645.
3. Gudjonsson, S., Davidsson, T., Mansson, W., *Incontinent urinary diversion.* BJU International, 2008. 102: p. 1320-1325,
4. Konety, B. R., Allareddy, V., *Influence post-cystectomy complications on cost and subsequent outcome.* Journal of Urology, 2007. 177: p. 280-287.
5. Dahl, D. M., McDougan, W. S., *Campbell-Walsh Urology, 9th Edition: Use of intestinal segments and urinary diversion.*, ed. A. J. Wein, Kavoussi, L. R., Novick, A. C. 2009.
6. Niklason, L. E., Gao, J., Abbott, W. M., Hirschi, K., Houser, S., Marini, R., Langer, R., *Functional arteries grown in vitro.* Science, 1999. 284: p. 489-493.
7. Poh, M., Boyer, M., et al., *Blood vessels engineered from human cells.* The Lancet, 2005. 365: p. 2122-2124.
8. Niklason, L. E., Yeh, A. T., Calle, E. A., Bai, Y., Valentin, A., Humphrey, J. D., *Enabling tools for engineering collagenous tissues integrating bioreactors, intravital imaging, and biomechanical modeling.* Proceedings of the National Academy of Sciences, 2010. 107: p. 3335-3339.
9, Dahl, S. L. M., Koh, J., Prabhakar, V., Niklason, L. E., *Decellularized native and engineered arterial scaffolds for transplantation.* Cell Transplantation, 2003. 12: p. 659-666.
10. Dahl, S. L. M., Kypson, A. P., Sawson, J. H., Blum, J. L., Strader, J. T., Li, Y., Manson, R. J., Tente, W. E., DiBernardo, L., Hensley, M. T., Carter, R., Williams, T. P., Prichard, H. L., Dey, M. S., Begelman, K. G., Niklason, L. E., *Readily available tissue-engineered vascular grafts.* Science Translational Medicine, 2010. 3(Epub ahead of print).
11. Farnham, S. B., Cookson, M. S., *Surgical complications of urinary diversion.* World Journal of Urology, 2004. 22: p. 157-167.
12. Stein, J. P., *Improving outcomes with radical cystectomy for high-grade invasive bladder cancer.* World Journal of Urology, 2006. 24: p. 509-516.
13. Kouba, E., Sands, M., Lentz, A. Wallen, E. Pruthi, R. S., *Incidence and risk factors of stomal complications in patients undergoing cystectomy with deal conduit urinary diversion for bladder cancer.* Journal of Urology, 2007. 178: p. 950-954.
14. Shabsigh, A., Korets, R., Vora, K. C., Brooks, C. M., Cronin, A. M., Savage, C., Raj, G., Bochner, B. H., Dalbagni, G., Herr, H. W., Donat, S. M., *Defining early morbidity of radical cystectomy for patients with bladder cancer using a standardized reporting methodology.* European Urology, 2009. 55: p. 164-174.
15. Nazarko, L., *Urinary tract infection: diagnosis, treatment and prevention.* British Journal of Nursing, 2009. 18: p. 1170-1174.
16. Longley, J. R., Ravera, J., Riddell, O., Jeter, K., *Carbon urinary conduits.* A experiments. Investigative Urology, 1977, 15: p. 59-64.
17. Mansson, W., Harzmann, R., *Clinical experience with an alloplastic stoma prosthesis (Biocarbon) for urinary conduits and cutaneous ureterostomy.* Scandinavian Journal of Urology and Nephrology, 1988. 22: p. 223-226.
18. Basu, J., Guthrie, K., Hagan, R., Sangha, N., Genheimer, C., Quinlan, S., Payne, R., Rapoport, S., Knight, T., Wagner, B. J., Rivera, E., Jaoy, M. J., Jain, D., Bertram, T. A., Ludlow, J. W., *Functional de novo Neo-Urinary Conduit from Porcein peripheral blood and adipose-derived smooth muscle cells.*, in 7th Annual ISSCR Meeting. 2009: Barcelona, Spain.
19. Raya-Rivera, A. Esquilliano, D. R. Yoo, J. J., Lopez-Bayghen, E., Soker, S., Atala, A., *Tissue-engineered autologous urethras for patients who need reconstruction: an observational study.* Lancet, 2011. Mar. 7 (Epub ahead of print).
20. El-Kassaby, A. W., Retik, A. B., Yoo, J. J., Atala, A., *Urethral stricture repair with an off-the-shelf collagen matrix.* Journal of Urology, 2003. 169: p. 170-173.
21. Bodin, A., Bharadwaj, S., Wu, S., Gatenholm, P., Atala, A., Zhang, Y., *Tissue-engineered conduti using urine-derived stem cells seeded bacterial cellulose polymer in urinary reconstruction and diversion.* Biomaterials, 2010. 31: p. 8889-8901.
22. Hipp, J., Andersson, K. E., Kwon, T. G., Kwak, E. K., Yoo, J., Atala, A., *Microarray analysis of exstrophic human bladder smooth muscle.* BJU International, 2008. 101: p. 100-105.
23. Kim, B. S., Atala, A., Yoo., J. J., *A collagen matrix derived from bladder can be used to engineer smooth muscle tissue.* World Journal of Urology, 2008. 26: p. 307-314.
24. Tian, H., Bharadwaj, S., Liu, Y., Ma, P. X., Atala, A., Zhang, Y., *Differentiation of human bone marrow mesenchymal stein cells into bladder cells: potential for urological tissue engineering.* Tissue Engineering Part A, 2010. 16: p. 1769-1779.
25. Dahl, S. L. M., Kypson, A. P., Sawson, J. H., Blum, J. L., Strader, J. T., Li, Y., Manson, Tente, W. E., DiBernardo, L., Hensley, M. T., Carter, T. P., Prichard, H. L., Dey, M. S., Begelman, K. G., Niklason, L. E., *Readily available tissue-engineered vascular grafts.* Science Translational Medicine, 2011. (Epub ahead of print).
26. Backhaus, B. O., Kaefer, M., Haberstroh, K. M., Hite, K., Nagatomi, J., Rink, R. C., Cain, M. P., Casale, A., Bizios, R., *Alterations in the molecular determinants of bladder compliance at hydrostatic pressures less than 40 cm water.* Journal of Urology, 2002. 168: p. 2600-2604.

27. Hiles, M. C., Badylak, S. F., et al., *Porosity of porcine small-intestinal submucosa for use as a vascular graft*. Journal of Biomedical Materials Research, 1993. 27: p. 139-144.
28. Niklason, L. E., Abbott, W. A., Gao, J., Klagges, B., Hirschi, K. K., Ulubayram, K., Conroy, N., Jones, R., Vasanawala, A., Sanzgiri, S., Langer, R., *Morphologic and mechanical characteristics of bovine engineered arteries*. Journal of Vascular Surgery, 2001. 33: p. 628-638.
29. Woessner, J. F., *The determination of hydroxyproline in tissue and protein samples containing small proportions of this amino acid*. Archives of Biochemistry and Biophysics, 1961. 93: p. 440-447.
30. Taguchi, T., Ikoma, T., Tanaka, J., *An improved method to prepare hyaluronic acid and type II collagne composite matrices*. Journal of Biomedical Materials Research, 2002. 61: p. 330-336.
31. Stegman, S. J., Chu, S., Bensch, K., Armstrong, R., *A light and electron microscopic evaluation of Zyderm collagen and Zyplast implants in aging human facial skin*. A pilot study. Archives Dermatology, 1987. 123: p. 164.4-1649.
32. Spindel, E., Pauley, M., Jia, Y., Gravett, C., Thompson, S., Boyle, N., Ojeda, S., Norgren, R., *Leveraging human genomic information to identify nonhuman primate sequences for expression array development*. BMC Genomics, 2005. 6: p. 160.

The invention claimed is:

1. An artificial stented urinary conduit for implantation in a patient in need of urinary diversion and drainage, comprising:
a tubular, substantially acellular, extracellular matrix formed as a tube on a biodegradable scaffold, wherein the extracellular matrix was produced and secreted in vitro by non-autologous smooth muscle cells grown around a tubular, non-degradable stent such that the extracellular matrix totally envelopes and encases the stent on its inner and outer surfaces, wherein the extracellular matrix is rotationally fixed with respect to the stent.

2. The artificial urinary conduit of claim 1 wherein the tubular stent comprises metal.

3. The artificial urinary conduit of claim 1 wherein the tubular stent comprises a polymer.

4. The artificial urinary conduit of claim 1 wherein the tubular stent is perforated.

5. The artificial urinary conduit of claim 1 wherein the extracellular matrix forms a tubular tissue that is not subject to deconvolution.

6. The artificial urinary conduit of claim 1 wherein the artificial stented urinary conduit is manufactured using banked cells.

7. The artificial urinary conduit of claim 1 wherein the artificial stented urinary conduit is pre-manufactured prior to implantation.

8. The artificial urinary conduit of claim 1 wherein collagen comprises at least 20% of the extracellular matrix.

9. The artificial urinary conduit of claim 1 wherein collagen comprises at least 25% of the extracellular matrix.

10. The artificial urinary conduit of claim 1 wherein collagen comprises at least 30% of the extracellular matrix.

11. The artificial urinary conduit of claim 1 wherein the artificial urinary conduit has a rupture strength of greater than 1000 mm Hg and up to 2000 mm Hg.

* * * * *